(12) United States Patent
Huang et al.

(10) Patent No.: US 12,280,070 B2
(45) Date of Patent: Apr. 22, 2025

(54) DRUGS FOR PREVENTION OR TREATMENT OF SEPSIS

(71) Applicant: SOUTHEAST UNIVERSITY, Jiangsu (CN)

(72) Inventors: Wei Huang, Nanjing (CN); Haibo Qiu, Nanjing (CN); Ke Fang, Nanjing (CN); Jianfeng Xie, Nanjing (CN); Ling Liu, Nanjing (CN); Yi Yang, Nanjing (CN); Ran Yang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 18/955,967

(22) Filed: Nov. 21, 2024

(65) Prior Publication Data

US 2025/0082666 A1 Mar. 13, 2025

Related U.S. Application Data

(63) Continuation of application No. PCT/CN2024/072889, filed on Mar. 21, 2024.

(30) Foreign Application Priority Data

Jun. 28, 2023 (CN) .......................... 202310773883.9

(51) Int. Cl.
| | | |
|---|---|---|
| *A61K 31/7105* | (2006.01) | |
| *A61K 9/00* | (2006.01) | |
| *A61P 31/04* | (2006.01) | |

(52) U.S. Cl.
CPC ........ *A61K 31/7105* (2013.01); *A61K 9/0019* (2013.01); *A61P 31/04* (2018.01)

(58) Field of Classification Search
CPC .... A61K 31/7105; A61K 9/0019; A61P 31/04
USPC ..................... 435/6.1, 91.1, 91.31, 455, 458; 514/44 A, 44 R; 536/23.1
See application file for complete search history.

(56) References Cited

FOREIGN PATENT DOCUMENTS

| CN | 111500710 A | 8/2020 |
|---|---|---|
| CN | 114181940 A | 3/2022 |
| CN | 115177734 A | 10/2022 |
| CN | 116814623 A | 9/2023 |

OTHER PUBLICATIONS

Beltrán-García, Jesús et al., Circular RNAs in Sepsis: Biogenesis, Function, and Clinical Significance, Cells, 9 (6): 1-20, 2020.
Li, Lian-Ju et al., Circular RNA Expression Profile and Potential Function of Hsa_circ_0045272 in Systemic Lupus Erythematosus, Immunology, 155: 137-149, 2018.
International Search Report in PCT/CN2024/072889 mailed on Apr. 10, 2024, 12 pages.
Written Opinion in PCT/CN2024/072889 mailed on Apr. 10, 2024, 9 pages.

*Primary Examiner* — Jane J Zara
(74) *Attorney, Agent, or Firm* — Porus IP LLC

(57) ABSTRACT

A drug for the prevention or treatment of sepsis is provided. The drug comprises an exosome containing a circRNA MOTOR, and a nucleotide sequence corresponding to the circRNA MOTOR is shown in SEQ ID NO: 1.

3 Claims, 4 Drawing Sheets

Specification includes a Sequence Listing.

DRUGS FOR PREVENTION OR TREATMENT OF SEPSIS

CROSS-REFERENCE TO RELATED APPLICATION

This application is a Continuation of International Application No. PCT/CN2024/072889, filed Mar. 21, 2024, which claims priority to Chinese Patent Application No. 202310773883.9, filed on Jun. 28, 2023, the entire contents of each of which are hereby incorporated by reference.

SEQUENCE LISTING

The instant application contains a Sequence Listing which has been submitted electronically in XML format and is hereby incorporated by reference in its entirety. The XML copy, created on Oct. 22, 2024, is named "2024-10-22-Sequence Listing-68402-H005US00," and is 8,192 bytes in size.

TECHNICAL FIELD

The present disclosure generally relates to the field of gene technology for circRNA-encoded small peptides, and particularly relates to drugs for the prevention or treatment of sepsis.

BACKGROUND

Sepsis is a life-threatening condition characterized by organ dysfunction due to an abnormal response to infection, representing a significant health risk. A multicenter cross-sectional study in China found that approximately 20.6% of ICU admissions are due to sepsis, with a staggering 90-day mortality rate of 35.5%. Thus, a comprehensive investigation into the pathogenesis of sepsis and the identification of new therapeutic targets are critical for advancing prevention and treatment, which posses a major clinical challenge.

Immune dysregulation is a fundamental mechanism in sepsis development. While excessive inflammatory responses contribute to multi-organ damage, sepsis is often marked by prolonged immunosuppression. A key feature of this immunosuppression is lipopolysaccharide (LPS) tolerance in monocytes. LPS-tolerant monocytes exhibit diminished abilities to internalize and eradicate pathogens, leaving patients vulnerable to secondary infections, which are a leading cause of mortality in sepsis. However, the precise mechanisms underlying LPS tolerance in monocytes remain unclear, and there is a notable absence of molecular therapies to modulate this tolerance—an urgent area for research.

Accordingly, it is desired to provide a drug for the prevention or treatment of sepsis.

SUMMARY

One or more embodiments of the present disclosure provide a drug for the prevention or treatment of sepsis, wherein the drug comprises an exosome containing a circRNA MOTOR, wherein a nucleotide sequence corresponding to the circRNA MOTOR is shown in SEQ ID NO: 1.

In some embodiments, a dosage form of the drug is at least one of a tablet, a capsule, an oral liquid, a lozenge, an aerosol, an injection, an ointment, or a granule.

In some embodiments, the dosage form of the drug is the injection.

BRIEF DESCRIPTION OF THE DRAWINGS

The present disclosure will be further illustrated by way of exemplary embodiments, which will be described in detail through the accompanying drawings.

These embodiments are not limiting, and in these embodiments the same numbering indicates the same structure, wherein.

DETAILED DESCRIPTION

Figure 1:
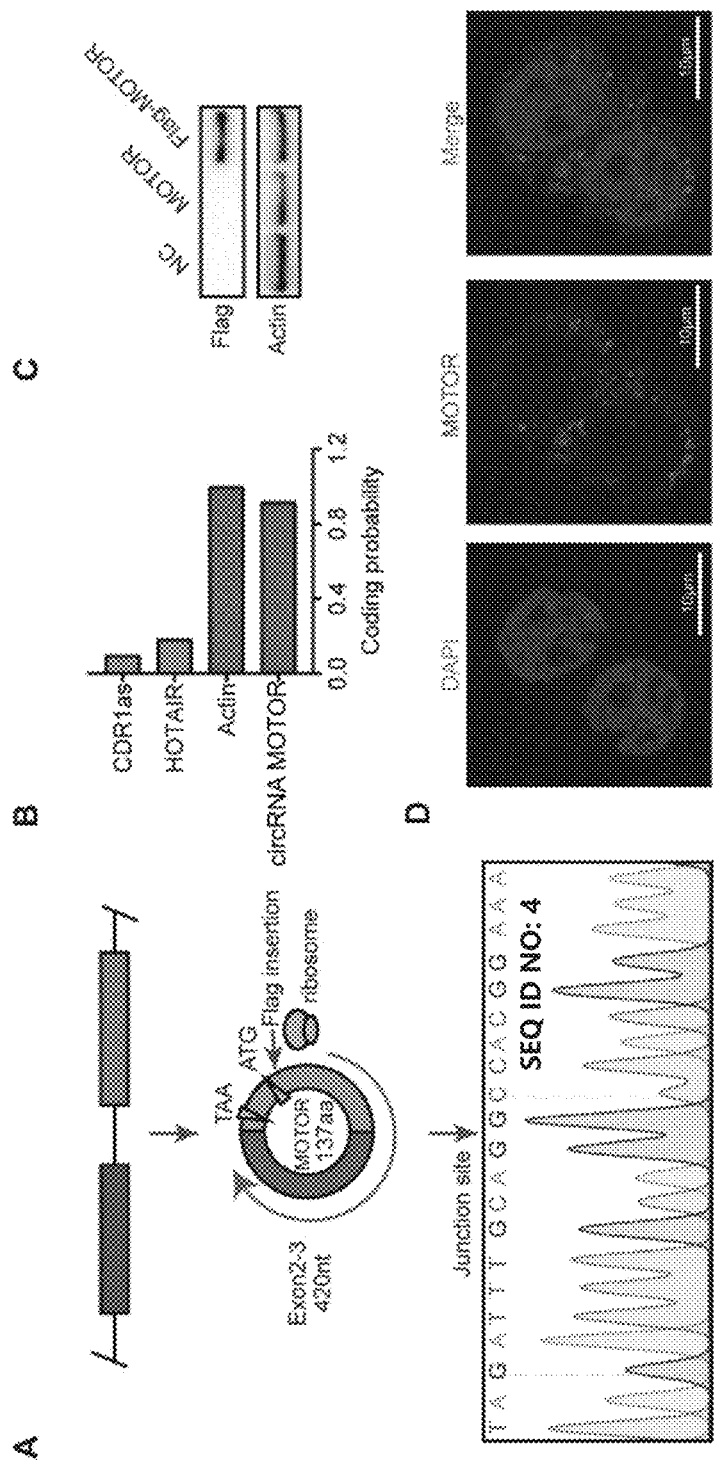
FIG. 1 is a schematic diagram illustrating an exemplary structure of a small peptide encoded by circRNA MOTOR, and localized in the cytoplasm according to some embodiments of the present disclosure.

In order to provide a clearer understanding of the technical solutions of the embodiments described in the present disclosure, a brief introduction to the drawings required in the description of the embodiments is given below. It is evident that the drawings described below are merely some examples or embodiments of the present disclosure, and for those skilled in the art, the present disclosure may be applied to other similar situations without exercising creative labor, unless otherwise indicated or stated in the context, the same reference numerals in the drawings represent the same structures or operations.

It should be understood that, although the terms "first," "second," "third," etc., may be used in the present disclosure to describe various elements, these elements should not be limited by these terms. These terms are used solely to distinguish one element from another. For example, a first product may be referred to as a second product, and similarly, within the scope of exemplary embodiments of the present disclosure, the second product may be referred to as the first product.

Set forth in the present disclosure and the claims, unless explicitly indicated otherwise in the context, words such as "one," "a," "an," and/or "the" do not specifically denote the singular form and may also include the plural form. In general, the terms "comprising" and "including" only suggest the inclusion of steps and elements that have been explicitly identified, and these steps and elements do not constitute an exclusive listing; methods or devices may also include other steps or elements.

Unless otherwise defined, all technical and scientific terms used in the present disclosure have the same meaning as typically understood by those of ordinary skill in the art to which the present disclosure pertains.

One or more embodiments of the present disclosure provide drugs for the prevention or treatment of sepsis, the drug includes circRNA MOTOR-containing exosomes.

In some embodiments, the circRNA MOTOR is a circular RNA (circRNA) with coding ability, and the circRNA can be translated into a small peptide consisting of 137 amino acids (137aa).

In some embodiments, the nucleotide sequence of circRNA MOTOR is shown in SEQ ID NO: 1.

In some embodiments, a vector overexpressing hsa_circRNA_056558 (MOTOR) is constructed by molecular cloning based on the gene sequence of hsa_circRNA_056558, the vector is transfected into a cell, and exosomes produced by the cells are collected by ultracentrifugation, thereby obtaining the exosomes containing circRNA MOTOR.

Exosomes are nanoscale vesicles secreted by cells between 40 and 100 nm in size, which are able to load "cargo" and deliver it to target cells. Exosomes have unique advantages as natural endogenous carriers of drugs, such as their low immunogenicity, high stability in blood, high efficiency of drug transport to cells, and stronger enhanced permeation retention effect (EPR). Currently, exosomes have been successful in delivering other types of drugs such as gene-based drugs, anti-cancer drugs, and anti-inflammatory drugs. As gene-based drug carriers, exosomes help to simultaneously increase transfection efficiency and reduce side effects.

In some embodiments, conventional excipients are added to the drug to make a variety of pharmaceutically acceptable dosage forms according to conventional processes.

In some embodiments, the dosage form of the drug is at least one of a tablet, a capsule, an oral liquid, a lozenge, an aerosol, an injection, an ointment, or a granule.

In some embodiments, the dosage form of the drug is the injection.

Embodiments of the present disclosure provide a drug for the prevention or treatment of sepsis; the drug comprises exosomes containing the circRNA MOTOR. The circRNA MOTOR effectively reverses the lipopolysaccharide (LPS)—tolerant state of monocytes at the onset of sepsis. Its mechanism of action includes promoting the secretion of chemokines and pro-inflammatory cytokines, as well as enhancing the expression of antigen-presenting genes in monocytes during bacterial infections. This modulation of both innate and adaptive immune functions helps prevent secondary infections and ultimately improves the survival rates of septic patients.

The experimental techniques in the following examples, unless otherwise specified, are conventional techniques. The test materials used in the following examples, unless otherwise specified, are obtained from standard biochemical reagent companies. Quantitative assays in the following examples are performed with three replicate experiments, and the results are averaged.

EXAMPLES

Example 1. CircRNA MOTOR is a Circular RNA (circRNA, Also Referred as Hsa_circRNA_056558) with Coding Ability and can be Translated into a Small Peptide of 137 Amino Acids (137aa)

1.1 CircRNA MOTOR was identified as a circRNA by PCR and Sanger sequencing, and bioinformatics was used to predict the coding ability of circRNA MOTOR. The coding ability and subcellular localization of circRNA MOTOR was verified by western blot and immunofluorescence, and it was found that circRNA MOTOR could be translated into small peptides localized in the cytoplasm (see FIG. 1).

1.1.1 PCR and Sanger Sequencing Experiments (1) RNA Extraction a) Preparation of required reagents and consumables: Trizol; chloroform; isopropanol; DEPC water; RNase-free pipette tips of different sizes; 1.5 mL RNase-free EP tubes.

(b) The specific steps were as follows: human monocyte THP1 was collected in EP tubes, 1 mL of Trizol was added to each EP tube, and the cells were blown repeatedly with a pipette until no cell precipitation could be seen; the centrifuge was pre-cooled to 4° C., and 0.2 mL of chloroform was added to each EP tube, which was vortexed for 15 s and then left to stand at room temperature for 5 min; the cells were then centrifuged for 15 min at 12,000 rcf, divided into three layers, the upper layer was colorless aqueous RNA, and the middle and lower layers were organic phenol chloroform layer. The EP tube was carefully took out, 0.4 mL of supernatant was vertically aspirated, 0.5 mL of isopropanol was added, the mixture was inverted and mixed 10 times, and left to stand at room temperature for 10 min and centrifuged 12,000 rcf for 10 min. Supernatants were discarded, and 75% ethanol (prepared with DEPC water) was added and mixed by inversion. After centrifugation at 7500 rcf for 5 minutes, supernatants were discarded. After centrifugation at 7500 rcf for 5 minutes, supernatants were discarded. After brief centrifugation for 15 seconds, supernatants were discarded, and RNA precipitates were retained. 30 μL of DEPC water was added to dissolve the RNA precipitates. A concentration of RNA precipitates was measured by a spectrophotometer and the concentration of RNA precipitates was adjusted to 1 ng/μL with DEPC water.

(2) Reverse Transcription PCR 500 ng of RNA was subjected to reverse transcription PCR using a reverse transcription kit (PrimeScript™ RT reagent Kit with gDNA Eraser, TAKARA, RR047A).

(3) PCR

The cDNA obtained by reverse transcription in the previous step was diluted threefold with RNase-free water and then prepared according to the following system:

| | |
|---|---|
| 2× PCR buffer for KOD FX | 25.0 μL |
| Primer 1 (10 μM) | 0.4 μL |
| Primer 2 (10 μM) | 0.4 μL |
| 2 mM dNTPs | 10.0 μL |
| Template DNA/cDNA | 2.0 μL |
| KOD FX (1.0 U/μL) | 1.0 μL |
| ddH$_2$O | To 20.0 uL |

The PCR primer sequences were as follows:

| | |
|---|---|
| MOTOR-F (SEQ ID NO: 2) | GGCAGAAGTGAAAGATACAACC |

| | |
|---|---|
| MOTOR-R (SEQ ID NO: 3) | ACTCCTCCTGCCAGATTACAGAT |

After preparation of the PCR system, the reaction was performed using a Bio-Rad PCR instrument. The PCR products were sent to Shanghai Biotech for Sanger sequencing.

1.1.2 Western Blot Experiment (1) Protein Extraction a) Preparation of required reagents and consumables: Radio Immunoprecipitation Assay (RIPA) protein lysate; Cocktail protease inhibitor; sterilized 1.5 mL EP tubes.

(b) The specific steps were as follows: the FLAG-MOTOR plasmid was transfected into the cells in a 12-well plate, 100 µL of RIPA and Cocktail inhibitor were added and incubated on ice for 10 minutes, centrifuged at 12000 rpm and 4° C. for 20 minutes to take a supernatant, which contains the desired protein. 5× loading buffer was added to the supernatant and heated at 100° C. for 5 minutes to obtain boiled protein samples.

(2) Immunoblotting Experiment a) Gel preparation: 12% SDS-PAGE gels were prepared using the 12% PAGE Gel Rapid Preparation Kit (Bio-rad; 64484826):

1.3 µL of TEMED and 30 µL of 10% AP were added to 3 mL of Resolver A and Resolver B solutions respectively. After shaking and mixing, the mixtures were injected into the gel preparation glass plate such that a distance between the liquid level and the upper edge of the short glass plate was only 0.5 cm longer than the comb teeth. 2 µL of TEMED and 10 µL of 10% AP were added to 1 mL of Stack A and Resolver B solutions respectively. After shaking and mixing, the mixtures were injected into the gel preparation glass plate and the comb teeth were inserted.

2. After waiting for 30 minutes, when the upper layer of gel solidified, the comb teeth were removed, and electrophoresis could be carried out.

b) Electrophoresis

1. The solidified gel plate was placed in the electrophoresis tank and enough 1× Running buffer was added.

2. The boiled protein samples were vortex-mixed and centrifuged instantaneously. 5 µL of molecular weight protein standard and 15 µL of protein samples were added to the spotting wells, respectively.

3. The electrophoresis conditions were set as: constant voltage of 200 v for 45 minutes.

c) Transfer to Membrane

1. PVDF membranes of the corresponding sizes were cut according to the target bands, and the membranes were activated with methanol for 10 min.

2. At the end of the electrophoresis, the glass plate was pried open with a gel opener, and the separating gel was cut off and placed in the transmembrane buffer.

3. The sandwich method was used to transfer the membrane, the specific steps were as follows: a sponge pad, three layers of filter paper, PVDF membrane, separating gel, three layers of filter paper, and sponge pad were placed in turn on the positive side (white), and finally connected to the negative side (black). The whole process was carried out in the transfer buffer. Careful handling was required, and layers were gently rolled to remove bubbles.

4. The membrane transfer conditions were set as: constant current 300 mA for 60 min, and 1× transfer buffer was added. Since heat would be generated during the transfer process, the transfer tank needed to be placed in a low-temperature environment.

d) Blocking

1. The membrane was placed in the pre-prepared blocking solution (2.5 g bovine serum albumin+50 mL 1×TBST) and blocked on a shaker at room temperature for 1 hour.

f) Immune Reaction

1. The surface blocking solution was slowly washed away with 1× TBST.

2. The primary antibody was prepared (5 µL FLAG primary antibody+10 mL 1×TBST) and added to the incubation box so that the membrane could gently shake with the shaker in the box and was incubated overnight at 4° C.

3. The primary antibody was recovered, and the membrane was washed three times using 1× TBST for 7 min each time, after which the secondary antibody was incubated at room temperature for 60 min, the secondary antibody was recovered, and the membrane was washed three times using 1× TBST for 7 min each time. The membrane was immersed in 1× TBST solution for the next step.

g) Color Reaction

1. The Eblot Ultrasensitive Fully Automated Luminescence Imaging Analyzer System was turned on.

2. The luminescent solution A and luminescent solution B were mixed in a ratio of 1:1. The mixture was spread on the membrane using a pipette for exposure and photography.

The results showed that Flag-MOTOR can be detected, indicating that MOTOR can encode proteins.

1.1.3 Immunofluorescence Staining (1) Primary Antibody Incubation

Flag-MOTOR THP1 cells were harvested and fixed with 4% paraformaldehyde (PFA) for 1 h at room temperature, and subsequently rinsed with PBS 3 times for 5 min each. After being blocked with Blocking medium (1% fetal bovine serum+0.5% Tritonx-100) for 1 h at room temperature, Flag antibody diluted in PBS (1:200) was added and incubated at 4° C. overnight to obtain samples.

(2) Secondary Antibody Incubation

The samples were rinsed 3 times using PBS for 5 min each time. The corresponding secondary antibodies were diluted with PBS at a ratio of 1:400, and DAPI was diluted at a ratio of 1:1000. After incubation for 1 h at room temperature, each sample was rinsed with PBS 3 times for 5 min each. The slices were sealed using nail polish; and images were acquired using confocal microscopy.

The results showed that Flag-MOTOR is mainly present in the cytoplasm.

In summary, circRNA MOTOR can be translated into small peptides localized in the cytoplasm. FIG. 1 presents circRNA MOTOR as a coding circRNA. FIG. 1A shows the structure schematic of circRNA MOTOR and the generation sequencing results of the junction site (the sequence of the junction site is shown in SEQ ID NO: 4). As shown in FIG. 1A, the nucleotide sequence corresponding to circRNA MOTOR is 420 nt in length and includes 2-3 exons. A cross-junction ORF (Open Reading Frame) encoded a 137aa peptide was identified. ATG is a translation initiation codon and TAA is a translation termination codon. The short arrow represents Flag insertion. Next to circRNA MOTOR is ribosome. FIG. 1B shows the coding ability of the RNA predicted by bioinformatics. Among them, CDR1 as and HOTAIR are classic circRNA and long non-coding RNA (lncRNA) that have been proven not to encode proteins and function in the form of RNA, respectively. Actin is a definite protein-coding gene. FIG. 1C shows that Flag-MOTOR can be detected by Flag antibody through western blot. FIG. 1D shows the immunofluorescence result of Flag-MOTOR.

Example 2 Knockdown of MOTOR Inhibits LPS-Stimulated Chemokine and Pro-Inflammatory Cytokine Release from Monocytes 2.1 Human monocyte THP1 cells were cultured in vitro. SiRNAs specifically targeting circRNA MOTOR were ordered. The siRNAs targeting MOTOR and control siRNAs were transfected into the THP1 cells using the NEON electroporation system. At 24 h after transfection, 1 µg/mL LPS was added to the cells, and the cells were harvested after 24 h treatment with LPS. The expression of cytokines and antigen presentation-related factors was detected by next-generation sequencing and qPCR. In this regard, chemokines include CCL8, CCL7, CXCL9, CXCL10, CXCL11, CXCL13, CCL2, CCL20, CCL4, CCL4L2, CCL3, CCL3, CXCL3, CCL3L3, CXCL2, CCL9, CXCL8, CXCL1, CCL5; cytokines include: IL6, IL33, IL1B, IL411, IL1RN, IL32, IL7R, IL18R1, IL15RA; surface molecules include: CD48, CD80, CD163 CD14, CD53, CD40, CD83, CD209; transcription factors include: ETV7, HESX1.

2.1.1 Next-Generation Sequencing and Analysis (1) The cells were collected, centrifuged at 500 rcf for 5 min at room temperature, the medium was discarded, and the cell sediment was washed once with PBS and 1 mL of Trizol was added.

(2) The cell-containing Trizol samples were quickly frozen in liquid nitrogen for 30 s and sent to a sequencing company on dry ice for next-generation sequencing.

(3) After the company returned the sequencing data, the expression of chemokines and pro-inflammatory factors was analyzed. The FPKM and z-score algorithms were used for normalization treatment, and a heatmap was made to reflect the expression differences of relevant genes.

2.1.2 qPCR (1) The qPCR system was formulated as the following table.

| | |
|---|---|
| cDNA | 2 μL |
| SYBR | 5 μL |
| F-primer | 0.2 μL |
| R-primer | 0.2 μL |
| ddH2O | 2.6 μL |
| Total | 10 μL |

The CT values were obtained after qPCR. The expression levels of the chemokines and pro-inflammatory factors were calculated based on the CT values.

Figure 2:
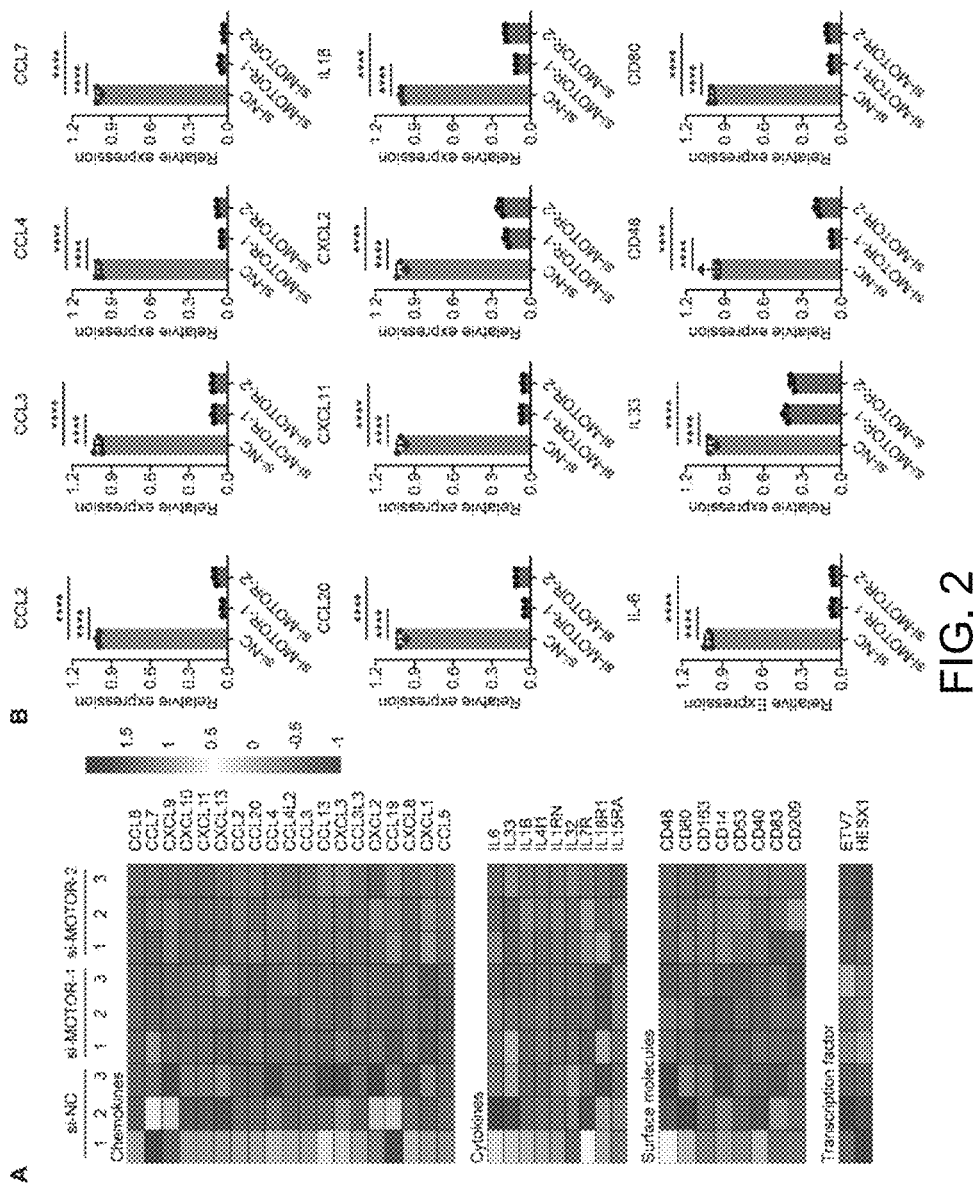
FIG. 2 is a graph illustrating knockdown of MOTOR inhibiting the expression of inflammatory factors and chemokines according to some embodiments of the present disclosure.

The results showed that knockdown of MOTOR using siRNA (si-MOTOR-1 and si-MOTOR-2) can significantly reduce the expression levels of chemokines and pro-inflammatory factors in both next-generation sequencing and qPCR assays, as shown in FIG. 2. Among them, si-NC is a control group. FIG. 2A shows the result of RNA-seq and FIG. 2B shows the result of qPCR.

Example 3 Overexpression of MOTOR Promotes LPS-Stimulated Release of Chemokines and Pro-Inflammatory Cytokines from Monocytes MOTOR was overexpressed in monocytes using lentiviral infection, and qPCR was used to detect the effect of LPS-stimulated overexpression of MOTOR on the release of cytokines from monocytes.

3.1 Lentivirus Packaging and Purification (1) HEK293T cells were co-transfected with vesicular stomatitis virus glycoprotein (vsvg), regulator of expression of virion proteins (rev), group-specific antigen (gag) and Flag-MOTOR plasmids, wherein a nucleotide sequence of the biological factor MOTOR encoded by the FLAG-MOTOR plasmid is shown as SEQ ID NO: 1.

(2) After 48 hours of transfection, supernatants in the petri dish were collected and replaced with fresh DMEM culture medium containing 1% FBS. After 96 hours, a second collection of the supernatants was performed.

(3) Virus concentrate with a volume of ⅕ of the supernatants were added and mixed, and left to stand overnight at 4° C.

(4) The supernatants with virus concentrate were centrifuged at 4° C., 11,000 rcf for 30 min, supernatants were discarded, and precipitates were the virus particles. The virus was resuspended with 1.5 mL of DMEM medium and stored at −80° C. in a refrigerator.

3.2 Lentivirus Infection (1) $2 \times 10^5$ THP1 cells were taken and placed in a 12-well plate, and 500 μL of virus solution was added and cultured in a cell incubator.

(2) One week after infection, puromycin was added for screening, and the screened cells were the cells overexpressing MOTOR (MOTOR OE).

3.3 Detection of Chemokines and Pro-Inflammatory Cytokines (1) MOTOR OE and control cells were stimulated with 1 μg/mL of LPS, and the cells were collected by centrifugation after 24 h for RNA extraction.

(2) The expression of chemokines and pro-inflammatory cytokines was detected using qPCR.

Figure 3:
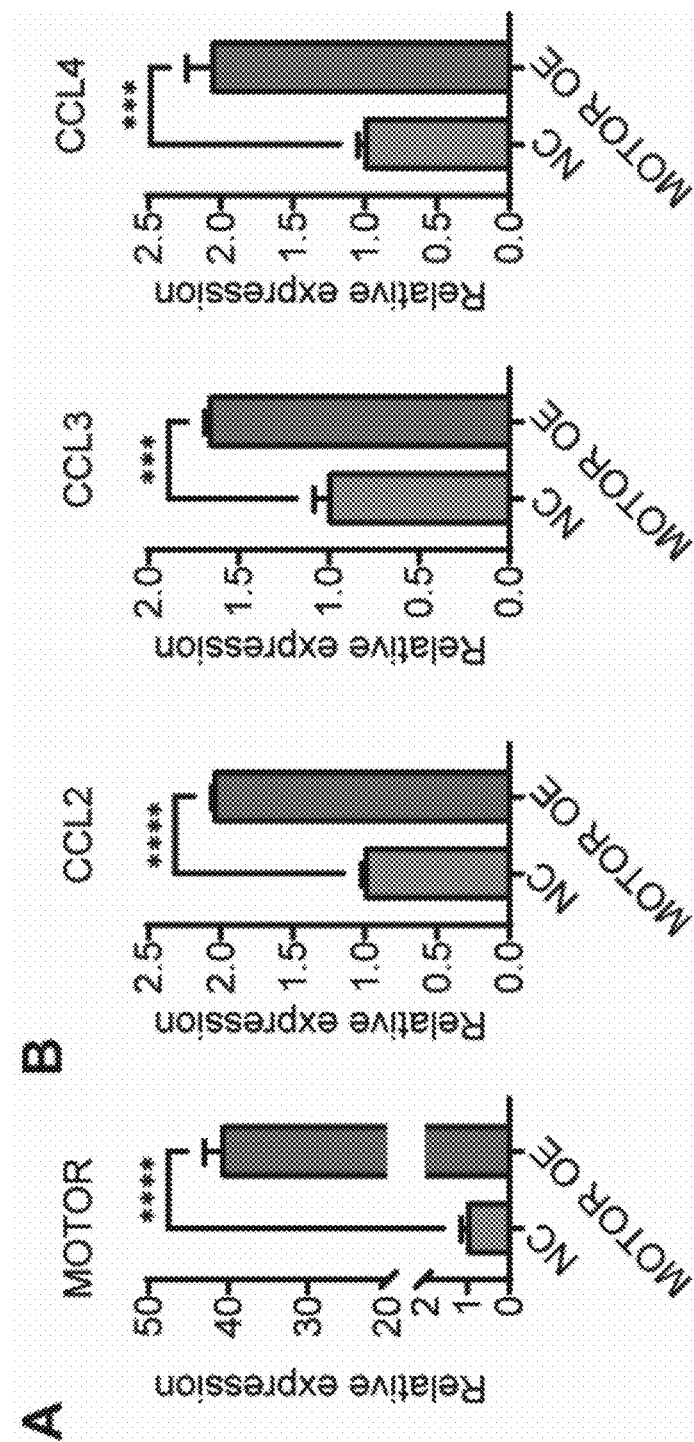
FIG. 3 is a graph illustrating overexpression of MOTOR promoting the expression of inflammatory factors and chemokines according to some embodiments of the present disclosure.

The results showed that overexpression of MOTOR can significantly increase an expression of chemokines and pro-inflammatory cytokines, and promote a response of monocytes to LPS, as shown in FIG. 3. FIG. 3A demonstrates the expression level of MOTOR after overexpression of MOTOR; FIG. 3B demonstrates mRNA levels of CCL2, CCL3 and CCL4 under LPS stimulation after overexpression of MOTOR detected by qRT-PCR.

Example 4 Exosome Containing CircRNA Motor Prolongs Survival in Septic Mice

The exosomes overexpressing MOTOR were collected and injected into septic mice by tail-vein injection, which in turn was observed for its effect on the survival time of septic mice.

4.1 Extraction of Exosomes Containing circRNA MOTOR (1) The supernatants of 293T cells and 293T cells overexpressing MOTOR were collected. The following steps were carried out sequentially: after centrifugation at 500 g for 5 min, precipitates were discarded, and supernatants were retained. After centrifugation at 2,000 g for 5 min, precipitates were discarded, and supernatants were retained. After centrifugation at 12,000 g for 30 min, precipitates were discarded, and supernatants were retained. After centrifugation at 200,000 g for 90 min, supernatants were discarded, and precipitates were retained; the precipitates were resuspended in PBS, and then centrifuged again at 200000 g for 90 minutes, supernatants were discarded, and precipitates were retained and finally resuspended with 200 μL PBS.

(2) Negative staining and electron microscopic photographs were performed.

4.2 Exosomes containing circRNA MOTOR and control exosomes were injected into septic mice to observe the survival time of mice.

4.2.1 Cecum ligation and puncture (CLP) is used to establish a mouse model of sepsis:

(1) C57BL/6 wild-type mice (male, 6-7 weeks old, weighing 20-29 g) were selected. The animals were anesthetized, and the cecum ligation was performed by cutting approximately 0.5 cm below the raphe in the midline of the abdomen at a point approximately 1 cm below the raphe, probing the cecum and slowly retracting it outside of the abdominal cavity. The cecum was punctured twice in the middle of the ligated segment, and after confirming that there was no obvious hemorrhage, the cecum was properly returned to the abdomen, and 1 mL of 0.9% saline was subcutaneously injected for anti-shock treatment. After the operation, the mice were allowed to eat and drink freely, and the room temperature was kept constant.

(2) Exosomes were diluted with PBS to contain 1×109 exosomes per 200 μL. At the 24th, 48th, and 72nd h after the establishment of the septic model, 200 μL of exosome solution was injected into mice by tail vein injection.

(3) The time of the first exosome injection was recorded as 0 h. The survival of the mice was observed and recorded every 24 h.

Figure 4:
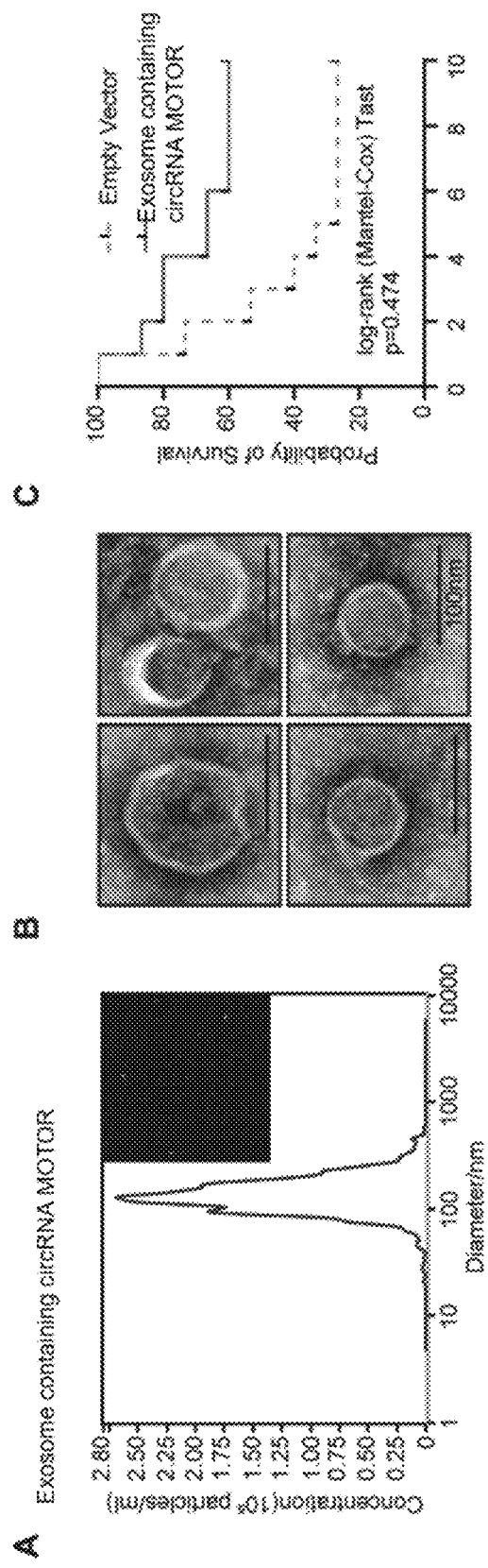
FIG. 4 is a graph illustrating the particle size analysis of exosomes containing a circRNA MOTOR and the results of the effect of exosomes circRNA containing MOTOR on prolonging the survival time of septic mice according to some embodiments of the present disclosure.

The results in FIG. 4 showed that injection of exosomes containing circRNA MOTOR can significantly prolong a survival time of septic mice. FIG. 4A and FIG. 4B show results by nanoparticle tracking analysis (NTA) and electron microscopy, respectively, indicating the successful extraction of exosomes using the described method. FIG. 4C demonstrates that injection of exosomes containing circRNA MOTOR into mice using tail vein injection is found to significantly prolong the survival time of septic mice. Empty vector is a control group.

The basic concepts have been described above, and it is apparent to those skilled in the art that the foregoing detailed disclosure is intended as an example only and does not constitute a limitation of the present disclosure. Although not expressly stated herein, those skilled in the art may make various modifications, improvements, and amendments to the present disclosure. Such modifications, improvements, and amendments are suggested in the present disclosure, so such modifications, improvements, and amendments remain within the spirit and scope of the exemplary embodiments of the present disclosure.

At the same time, specific terms are employed to describe the embodiments of the present disclosure. Terms e.g., "an embodiment," "one embodiment," and/or "some embodiments" are intended to refer to one or more features, structures, or features associated with at least one embodiment of the present disclosure. Thus, it should be emphasized and noted that the terms "an embodiment," "one embodiment," or "an alternative embodiment," mentioned at different locations in the present disclosure two or more times, do not necessarily refer to a same embodiment. Additionally, certain features, structures, or features of one or more embodiments of the present disclosure may be appropriately combined.

Some embodiments use numbers to describe the number of components, and attributes, and it should be understood that such numbers used in the description of the embodiments are modified in some examples by the modifiers "about", "approximately", or "generally". Unless otherwise stated, "about", "approximately" or "generally" indicates that a variation of ±20% is permitted. Accordingly, in some embodiments, the numerical parameters used in the present disclosure and claims are approximations, which may change depending on the desired features of the individual embodiment. In some embodiments, the numeric parameters should be considered with the specified significant figures and be rounded to a general number of decimal places. Although the numerical domains and parameters configured to confirm the breadth of their ranges in some embodiments of the present disclosure are approximations, in specific embodiments such values are set as precisely as possible within the feasible range.

With respect to each patent, patent application, patent application disclosure, and other material, e.g., articles, books, manuals, publications, documents, etc., cited in the present disclosure, the entire contents thereof are hereby incorporated herein by reference. Application history documents that are inconsistent with or conflict with the contents of the present disclosure are excluded, as are documents (currently or hereafter appended to the present disclosure) that limit the broadest scope of the claims of the present disclosure. It should be noted that in the event of any inconsistency or conflict between the descriptions, definitions, and/or use of terminology in the materials appended to the present disclosure and those described in the present disclosure, the descriptions, definitions, and/or use of terminology in the present disclosure shall prevail.

In closing, it should be understood that the embodiments described in the present disclosure are intended only to illustrate the principles of the embodiments of the present disclosure. Other deformations may also fall within the scope of the present disclosure. Thus, by way of example and not limitation, alternative configurations of embodiments of the present disclosure may be considered consistent with the teachings of the present disclosure. Accordingly, the embodiments of the present disclosure are not limited to the embodiments expressly presented and described herein.

What is claimed is:

1. A drug for the prevention or treatment of sepsis, wherein the drug comprises an exosome containing a circRNA MOTOR, wherein a nucleotide sequence corresponding to the circRNA MOTOR is shown in SEQ ID NO: 1.

2. The drug of claim 1, wherein a dosage form of the drug is at least one of a tablet, a capsule, an oral liquid, a lozenge, an aerosol, an injection, an ointment, or a granule.

3. The drug of claim 2, wherein the dosage form of the drug is the injection.

* * * * *

SEQUENCE LISTING

```
Sequence total quantity: 4
SEQ ID NO: 1            moltype = DNA  length = 420
FEATURE                 Location/Qualifiers
source                  1..420
                        mol_type = genomic DNA
                        organism = Homo sapiens
SEQUENCE: 1
gctccctgta gaattcgaaa ataacctttt ctaatgagga tgtctgatac tgttactgta   60
aaagatgaaa ctgcaacaat gaaggatttg gaggcagaag tgaaagatac aaccagagtt  120
gaaaatctta tcaaatcaga aaactatggg aagattttgg tagagaagaa tgaacattgt  180
attgagaaca atatagattt gcaggccacg gaaaggtatg atatatttga tccaagacag  240
tccattccag tccgggaatc tacagtggtg acaaggacat gggactcctc ctgccagatt  300
acagatggtt cactacagtt gacatcctgg ctgacaactg tgaaaaagaa ccttggatta  360
ttttatttta tttttgtggg acaccacaat cccaaatcca aaggacgcat caggcttcaa  420

SEQ ID NO: 2            moltype = DNA  length = 22
FEATURE                 Location/Qualifiers
source                  1..22
                        mol_type = other DNA
                        organism = synthetic construct
SEQUENCE: 2
ggcagaagtg aaagatacaa cc                                            22

SEQ ID NO: 3            moltype = DNA  length = 23
FEATURE                 Location/Qualifiers
```

```
source          1..23
                mol_type = other DNA
                organism = synthetic construct
SEQUENCE: 3
actcctcctg ccagattaca gat                                    23

SEQ ID NO: 4    moltype = DNA  length = 21
FEATURE         Location/Qualifiers
source          1..21
                mol_type = other DNA
                organism = synthetic construct
SEQUENCE: 4
tagatttgca ggccacggaa a                                      21
```